(12) United States Patent
Nguyen et al.

(10) Patent No.: US 10,662,269 B2
(45) Date of Patent: May 26, 2020

(54) ZIEGLER-NATTA CATALYZED POLYISOPRENE ARTICLES

(71) Applicant: LifeStyles Healthcare Pte. Ltd., Singapore (SG)

(72) Inventors: K C Nguyen, Dothan, AL (US); Chayapon Ngowprasert, A. Phunphin Suratthani (TH); Catherine Tang Kum Choo, Melaka (MY)

(73) Assignee: Lifestyles Healthcare PTE. Ltd., Singapore (SG)

( * ) Notice: Subject to any disclaimer, the term of this patent is extended or adjusted under 35 U.S.C. 154(b) by 0 days.

(21) Appl. No.: 16/115,750

(22) Filed: Aug. 29, 2018

(65) Prior Publication Data

US 2019/0062471 A1 Feb. 28, 2019

Related U.S. Application Data

(60) Provisional application No. 62/552,859, filed on Aug. 31, 2017.

(51) Int. Cl.
*C08F 36/08* (2006.01)
*A61F 6/04* (2006.01)

(52) U.S. Cl.
CPC .............. *C08F 36/08* (2013.01); *A61F 6/04* (2013.01)

(58) Field of Classification Search
CPC ...................................................... C08F 36/08
See application file for complete search history.

(56) References Cited

U.S. PATENT DOCUMENTS

| 3,215,649 A | 11/1965 | Preiss et al. |
| 3,494,781 A | 2/1970 | Knibbe et al. |
| 3,897,405 A | 7/1975 | Son et al. |
| 3,971,746 A * | 7/1976 | Hirai ........................ C08J 3/07 |
| | | 524/161 |
| 4,101,481 A | 7/1978 | Branlard et al. |
| 4,339,372 A | 7/1982 | Branlard et al. |
| 4,349,026 A | 9/1982 | Miyata |
| 4,406,853 A | 9/1983 | Miyata |
| 4,695,609 A | 9/1987 | Stevenson |
| 4,976,866 A | 12/1990 | Grinstead et al. |
| 5,149,436 A | 9/1992 | Taniguchi et al. |
| 5,254,635 A | 10/1993 | Stevenson et al. |
| 5,322,388 A | 6/1994 | Wells |
| 5,355,736 A | 10/1994 | Skogley |
| 5,677,382 A | 10/1997 | Tsuji et al. |

(Continued)

FOREIGN PATENT DOCUMENTS

| AU | 2009241426 A1 | 5/2012 |
| CN | 1479754 A | 3/2004 |

(Continued)

OTHER PUBLICATIONS

"Comparisons of cis-1,4-Polydienes," 11.5.4, Ionic and Coordinated Polymerizations, The Elements of Polymer Science & Engineering, Elsevier (2013), pp. 485-486. (Year: 2013).*

(Continued)

*Primary Examiner* — Catherine S Branch
(74) *Attorney, Agent, or Firm* — Servilla Whitney LLC (57) ABSTRACT

A polymeric article comprises an elastomeric layer comprising cured synthetic polyisoprene particles that comprise a Ziegler-Natta catalyzed polyisoprene.

18 Claims, 5 Drawing Sheets

(56) References Cited

U.S. PATENT DOCUMENTS

| | | | |
|---|---|---|---|
| 5,744,552 A | 4/1998 | D'Sidocky et al. |
| 5,773,499 A | 6/1998 | Umland et al. |
| 6,112,602 A | 9/2000 | Mitra |
| 6,114,469 A | 9/2000 | Rauchfuss et al. |
| 6,221,447 B1 | 4/2001 | Munn et al. |
| 6,288,181 B1 | 9/2001 | Ford et al. |
| 6,300,432 B1 | 10/2001 | Ford et al. |
| 6,313,236 B1 | 11/2001 | Ford et al. |
| 6,329,444 B1 | 12/2001 | McGlothlin et al. |
| 6,391,326 B1 | 5/2002 | Crepeau et al. |
| 6,401,547 B1 | 6/2002 | Hatfield et al. |
| 6,417,296 B2 | 7/2002 | Ford |
| 6,586,538 B2 | 7/2003 | Ford et al. |
| 6,618,861 B2 | 9/2003 | Saks et al. |
| 6,653,380 B2 | 11/2003 | Dzikowicz |
| 6,673,892 B2 | 1/2004 | Martinez et al. |
| 6,827,387 B2 | 12/2004 | Kolpasky |
| 6,828,387 B2 | 12/2004 | Wang et al. |
| 7,041,746 B2 | 5/2006 | Dzikowicz |
| 7,048,977 B2 | 5/2006 | Dzikowicz |
| 7,325,443 B2 | 2/2008 | Jonge et al. |
| 7,399,447 B2 | 7/2008 | Bowers et al. |
| 8,017,680 B2 | 9/2011 | Hill |
| 8,087,412 B2 | 1/2012 | Lucas et al. |
| 8,464,719 B2 | 6/2013 | Lucas |
| 9,074,027 B2 | 7/2015 | Lucas et al. |
| 9,074,029 B2 | 7/2015 | Lucas et al. |
| 9,725,539 B2 | 8/2017 | Lucas et al. |
| 2003/0161975 A1 | 8/2003 | Lucas et al. |
| 2004/0071909 A1 | 4/2004 | McGlothlin et al. |
| 2004/0164456 A1 | 8/2004 | McGlothlin et al. |
| 2004/0169317 A1 | 9/2004 | Wang et al. |
| 2007/0105971 A1 | 3/2007 | Schaller et al. |
| 2008/0105064 A1 | 5/2008 | Halland |
| 2009/0007704 A1 | 1/2009 | Bowers et al. |
| 2009/0084976 A1 | 4/2009 | Camilli |
| 2009/0234064 A1 | 9/2009 | Wang et al. |
| 2009/0272384 A1 | 11/2009 | Lucas et al. |
| 2010/0031759 A1* | 2/2010 | Tovena-Pecault ...... B01L 3/508 73/863.12 |
| 2011/0203227 A1 | 8/2011 | Chen et al. |
| 2016/0060437 A1 | 3/2016 | Naito et al. |
| 2016/0264753 A1* | 9/2016 | Salit .................... C08L 7/00 |
| 2017/0172786 A1* | 6/2017 | Nguyen .................. A61F 6/04 |
| 2017/0298159 A1 | 10/2017 | Lucas et al. |
| 2019/0031788 A1* | 1/2019 | Kodemura ............... C08C 1/00 |

FOREIGN PATENT DOCUMENTS

| | | | |
|---|---|---|---|
| CN | 1705687 A | 12/2005 |
| EP | 0086855 A1 | 8/1983 |
| GB | 2088389 A | 6/1982 |
| GB | 2436566 A | 10/2007 |
| KR | 101676714 B1 | 11/2016 |
| WO | 0177210 A2 | 10/2001 |
| WO | 2007017375 A1 | 2/2007 |
| WO | 2007113463 A1 | 10/2007 |
| WO | WO-2017159534 A1 * | 9/2017 | ............... C08C 1/00 |

OTHER PUBLICATIONS

NIPOL IR Product Sheet. (Year: 2014).*
Burfield et al., "Cold crystallization of natural rubber and its synthetic analogues," Polymer, 1987, vol. 28, pp. 907-910, p. 908. (Year : 1987).*
PCT International Search Report in PCT/SG2018/050442, dated Dec. 28, 2018, 6 pages.
PCT Written Opinion in PCT/SG2018/050442, dated Dec. 28, 2018, 6 pages.
Fordyce, David B., et al., "Intermolecular and Intramolecular Cross-Linking in Concentrated Polymer Solutions", Journal of the American Chemical Society.

* cited by examiner

ZIEGLER-NATTA CATALYZED POLYISOPRENE ARTICLES

CROSS-REFERENCE TO RELATED APPLICATIONS

This application claims priority under 35 U.S.C. § 119(e) to U.S. Provisional Application No. 62/552,859, filed Aug. 31, 2017, the disclosure of which is incorporated herein by reference in its entirety.

FIELD

The present disclosure is directed to personal protective articles and, more specifically, to condoms comprising polyisoprene catalyzed by Ziegler-Natta catalysts.

BACKGROUND

Prophylactic devices, such as condoms, finger cots, and gloves, such as examination and surgical gloves, are typically made of polymeric materials to provide protection against chemicals, abrasions, germs, viruses, and microbes among many uses. Polymeric materials include natural rubber latex (natural polyisoprene), synthetic polyisoprene, or various polyurethanes. Prophylactic devices made of natural rubber are strong. Natural rubber, sourced from *Hevea Brasiliensis* and/or guayule, has a high level of stereo-regularity, meaning that the polymer molecules of which it is comprised consist almost exclusively of cis-1,4 isoprene units. Natural rubber latex is also a highly branched polymer with a high molecular weight and a wide molecular weight distribution. These characteristics of the natural rubber result in vulcanized rubber products having a unique combination of strength and elasticity. However, natural rubber also contains proteins that produce dermal allergic reactions in some susceptible individuals.

Synthetic polyisoprene resins have been developed to provide the benefits of natural rubber and to eliminate the potential for protein allergy. However, some synthetic polyisoprenes, such as that produced by Kraton Inc., by anionic addition polymerization, typically consist of lower levels of stereo-regularity (i.e., less than 90% cis 1,4 isoprene) and reduced molecular weight. Consequently, articles produced from such synthetic polyisoprenes have inferior properties compared with natural rubber articles. In addition, synthetic polyisoprene latex with lower levels of stereo-regularity unfavorably flocks and agglomerates in suspension, which results in defects in dipped articles. A latex dip tank of such a synthetic polyisoprene correspondingly has a limited available processing window for dipping articles. Furthermore, addition of anti-flocculants interferes with cross-linking, resulting in anisotropic cure properties, e.g., poor strength and elongation properties, such as voids and cracks due to the formation of fractures in inter-particle and intra-particle regions.

There is an ongoing need to produce prophylactic devices, such as condoms, finger cots, and polymeric gloves that are thin, strong and non-allergenic.

SUMMARY

Embodiments according to the present disclosure include polymeric articles, and methods for manufacturing polymeric articles, that comprise synthetic polyisoprene materials catalyzed using Ziegler-Natta catalysts, substantially as shown in and/or described in connection with at least one of the figures, as set forth more completely in the claims, are disclosed. Various advantages, aspects, and novel features of the present disclosure will be more fully understood from the following description and drawings.

The foregoing summary is not intended, and should not be contemplated, to describe each embodiment or every implementation of the present disclosure. Other and further embodiments are described below.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments. It is to be understood that elements and features of one embodiment may be in other embodiments without further recitation. It is further understood that, where possible, identical reference numerals have been used to indicate comparable elements that are common to the figures.

DETAILED DESCRIPTION

Embodiments described in this disclosure, briefly summarized above and discussed in greater detail below, comprise polymeric articles, such as condoms, including thin-walled condoms and gloves. Embodiments may comprise condoms or gloves that are formed using coagulants. Embodiments may comprise condoms and gloves that are formed using Ziegler-Natta catalyzed synthetic polyisoprene materials. Embodiments may comprise condoms and gloves that are made using Ziegler-Natta catalyzed synthetic polyisoprene materials and coagulants.

The inventors have unexpectedly observed that condoms made from the Ziegler-Natta catalyzed polyisoprene resins described herein have enhanced tensile strength, allowing thinner condoms to be manufactured. Thinner condoms allow greater sensitivity to wearers. Thinner gloves are more flexible yet unexpectedly retain puncture resistance and abrasion resistance. Any, all or some of the embodiments according to the disclosure comprise condoms and/or polymeric gloves having a thickness of, for example, 0.030-0.065 mm in cross-sectional thickness. Exemplary embodiments according to the disclosure comprise condoms or polymeric gloves that are 0.040-0.055 mm in cross-sectional thickness.

Embodiments of the disclosure further comprise gloves, such as examination gloves, surgical gloves, and gloves for household use, and finger cots. Embodiments further comprise gloves that are formed using coagulants. Embodiments comprise a polymeric glove that includes a thumb having a front surface and a back surface; a plurality of fingers, a palm region; and a backhand region.

Figure 5:
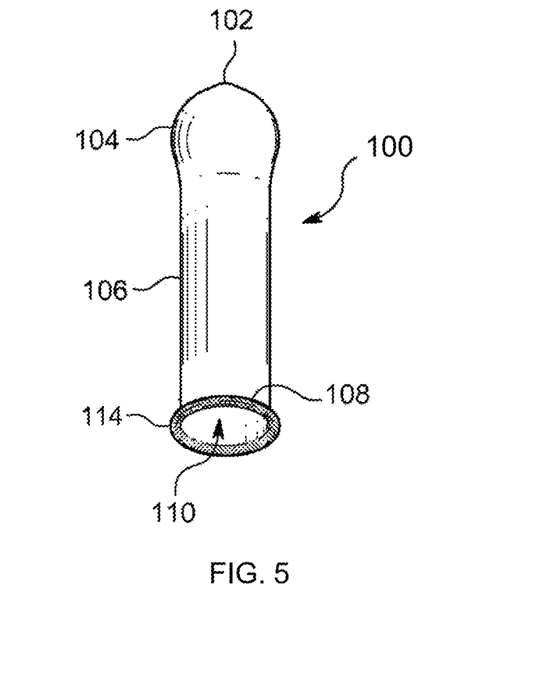
FIG. 5 is a perspective schematic view of a condom according to an embodiment.

Embodiments of the disclosure further comprise condoms. Embodiments further comprise condoms that are formed using coagulants. Embodiments comprise a condom that includes an open end, a closed end, and a tubular sheath extending from the closed end to the open end. FIG. 5 is a perspective schematic view of a condom according to an embodiment. The ZN catalyzed PI condom 100 disclosed herein comprises a closed end 104 and an open end 108. A tubular shaft 106 extends from the closed end 104 to the open end 108, which has an opening 110 opposite a teat end 102 of the closed end 104. Optionally, the condom further comprises a bead 114. The tubular shaft of the condom comprises the ZN catalyzed PI particles, which may be provided by an aqueous ZN catalyzed PI latex composition. The aqueous latex compositions may have a solids content in the range of 60% to 65% by weight. The compositions may further comprise additional water, preferably deionized water, to result in a composition solids content in the range of 55% to 60% by weight. Optionally, the aqueous latex compositions may further comprise one or more thickeners and/or stablizers/surfactants. Colorants and/or pigments may optionally be added to the aqueous latex compositions.

Before describing embodiments of the present disclosure in detail, the terminology used herein is for the purpose of describing particular embodiments only, and is not intended to be limiting. The embodiments described herein should not necessarily be limited to specific compositions, materials, designs or equipment, as such may vary. All technical and scientific terms used herein have the usual meaning conventionally understood by persons skilled in the art to which this disclosure pertains, unless context defines otherwise. Also, as used in this specification and the appended claims, the singular forms "a," "an," and "the" include plural referents unless the context clearly dictates otherwise.

The term "flexing" or "flex" refers to finger movements, such as bending fingers, making a fist, gripping, grasping, clenching or otherwise folding the fingers.

The terms "emulsion," "dispersion," "latex" and "suspension" are generally analogous and indicate a system in which small particles of a substance, such as rubber particles, are mixed with a fluid solvent (such as water and/or alcohols and/or other organic fluids) but are at least partially undissolved and kept dispersed by agitation (mechanical suspension) and/or by the molecular forces in a surrounding medium (colloidal suspension). Emulsions contemplated herein may further comprise typical and suitable components for rubber or elastomeric formulations and compounds, such as accelerators, such as guanidines, thiazoles, thiurams, sulfenamides, thioureas, dithiocarbamates, and xanthanates. Emulsions contemplated herein may further comprise activators, such as zinc oxides, cross-linking agents and curatives, such as elemental sulfur, mono-sulphidic donors, di-sulphidic donors, such as tetramethyl thiuram disulphide and tetraethyl thiuram disulphide; and/or polysulphidic donors, such as xanthogen polysulphide and dipentamethylene thiuramtetrasulfide. Emulsions contemplated herein may further comprise anti-oxidants and/or anti-ozonants. At least one suitable anti-oxidant is Wingstay L. Emulsions contemplated herein may further comprise, surfactants, such as sodium dodecyl sulfates and polyvinyl alcohols. Emulsions contemplated herein may further comprise rheology-modifiers, such as various clays and aluminosilicates, pH adjusters, such as hydroxides, such as potassium hydroxide, pigments, processing agents, and/or fillers as are known to those in the art.

The term "polymer" generally includes, but is not limited to, homopolymers, copolymers, such as for example, block, graft, random and alternating copolymers, terpolymers, etc. Furthermore, unless otherwise specifically limited, the term "polymer" includes all possible geometrical configurations of the molecule. These configurations include, but are not limited to isotactic, syndiotactic and random symmetries.

The term "thermoplastic" generally includes polymer materials that become reversibly pliable, moldable, and heatable above a specific temperature and solidify upon cooling. The term "thermoset" generally includes polymer materials that strengthen following heating and solidification, and cannot be reheated and re-formed after an initial forming. The term "thermoplastic elastomer" (TPE) denotes a class of copolymers comprising both thermoplastic and thermoset moieties, producing materials having properties of both moieties. The term "rubber" generally indicates elastomers produced from natural rubber latexes or synthetic elastomers.

A method for producing synthetic polyisoprene articles comprises using emulsions of synthetic polyisoprene resins catalyzed using Ziegler-Natta catalysts. Generally, synthetic polyisoprene particles of Ziegler-Natta catalyzed polyisoprene material comprise 96% cis-1,4-polyisoprene or more. The synthetic polyisoprene particles may comprise a median particle diameter in the range of approximately from 0.2 to 2 micrometers. Preferably from 0.2 to 1.5 micrometers. Exemplary synthetic polyisoprene materials are supplied by BST Elastomer Co., Ltd, located in Thailand. The method may further comprise a pre-vulcanization composition and post-vulcanization composition along with conventional emulsion additives, such as stabilizers, pH control agents, antioxidants, and preservatives, etc. A typical synthetic polyisoprene latex composition is provided in terms of 100 parts by weight of dry rubber (PHR). During compounding, the components of the latex composition may be suspended in aqueous and/or organic solvents.

In general, a pre-vulcanizing composition includes sulfur in the range of 0.6 to 1.8 PHR. An accelerator package includes zinc diethyldithiocarbamate (ZDEC) and/or zinc dibutyldithiocarbamate (ZDBC) accelerator, and/or sodium dibutyldithiocarbamate (SDBC) accelerator, a diisopropyl xanthogen polysulphide (DIXP) accelerator and/or a dipentamethylene thiuramtetrasulfide (DPTT) accelerator. The pre-vulcanizing composition may comprise a total accelerator content is in the range of 0.6 to 2.5 PHR. The pre-vulcanizing composition may comprise a zinc oxide activator. The pre-vulcanization composition may comprise a surfactant, i.e., a wetting agent. The surfactant may be a salt of a fatty acid, such as sodium stearate, sodium oleate, or potassium caprylate. Some embodiments comprise more than one surfactant, e.g., potassium caprylate, also known as potassium salt of octanic acid and sodium dodecyl benzene sulphonate (SDBS). Exemplary embodiments comprise a surfactant package having potassium caprylate, sodium dodecyl benzene sulphonate (SDBS) and polyoxyethylene cetyl/stearyl ether in the range of 0.3 to approximately 1.5 PHR. An anti-oxidant and preservative package includes a butylated reaction product of p-cresol and, optionally, dicyclopentadiene in the range of 0.3 to approximately 1.0 PHR.

The sulfur in the pre-vulcanizing package is, for example, elemental sulfur having a high soluble sulfur content, typically of the $S_8$ ring structure. The pre-vulcanization composition further comprises an accelerator. For example, an accelerator that can break or disrupt the $S_8$ sulfur ring structure is zinc dithiocarbamate. Reference to "high soluble sulfur content" means having enough soluble sulfur present to form sufficient to permeate into latex particles in the aqueous latex emulsion and crosslink during curing to achieve commercially acceptable articles, such as condoms and/or gloves. The pre-vulcanization of the synthetic latex particles in the latex occurs over a period of time, e.g., 9 hours to 2 days depending on the temperature of the latex, which is generally in the range of 20° C. to 30° C. The degree of pre-vulcanization at different points after initial compounding of the synthetic latex particles may be monitored by at least one of four tests. An equilibrium-swelling test, which uses any suitable solvent, measures the equilibrium swelling of films dried down from the synthetic latex. A relaxed modulus test gauges the vulcanization of the relaxed modulus at 100% extension (MR100) of films dried down from the dissolved latex. Similarly, a pre-vulcanized relaxed modulus test (PRM) measures the relaxed modulus at 100% extension of the pre-vulcanized films.

A Toluene Swell Index (TSI) test may be used to measure the level of crosslinking by immersing the dried casted film sample in the toluene and calculate the swollen rate. TSI may be substituted with an isopropanol index test. Cast film of the compounded latex to produce film thickness of 0.10-0.15 mm and dry the film at 50+/−3 degree Celsius for 10 minutes and/or leave the film at ambient temperature until it is fully dried. Peel off the film with the powder such as corn starch or $CaCO_3$ to prevent the film surface being stick to itself. Cut a disc sample with a die cutter. Submerge the disc film into the toluene for 60 minutes. Measure the diameter of the swollen film. Calculate the % swollen by subtract the original disc diameter from the swollen film diameter and divided by the original film diameter. The latex particles progress from a non-crosslink stage (index>220%), to a partial crosslink stage (index<220%), then to a semi-crosslink stage (index<180%) and finally to a fully crosslink stage (index<100%) as pre-vulcanizing sulfur is incorporated within the particle.

Compounding methods according to embodiments of the disclosure include dissolving a latex composition in an aqueous solvent and stirring periodically and examining for permeation of pre-vulcanization agents into the synthetic polyisoprene particles for example, by using an isopropanol index test. Polyisoprene latex has an inherent tendency to flock and 'case harden' due to a peripheral reaction with sulfur catalyzed by ZDBC or ZDEC, i.e., an outside surface hardens, preventing crosslinking of internal molecules. The presence of surfactants and creation of opened out $S_8$ chains of sulfur enables the diffusion of sulfur into the particles. In other words, the diffusion of sulfur into the particles, i.e., 'through-hardening' can occur, allowing the crosslinking of internal molecules. A latex article or product comprising a through-hardened structure is stronger than an otherwise similar latex article or product having a case-hardened structure.

The pre-vulcanization composition provides sulfur to synthetic polyisoprene latex particles in the aqueous synthetic polyisoprene emulsion for pre-vulcanizing the intra-particle regions. During pre-vulcanization, the ring structure of the sulfur is broken by the catalytic action of the accelerator, e.g., zinc dithiocarbamate, which penetrates the polyisoprene particles and initially interacts with the isoprene double bonds therein.

Without intending to be bound by theory, it is believed that the penetration of the components of the pre-vulcanizing composition into the polyisoprene particles is a function of the diffusion process, which may be a linear function of time. The penetration of the components comprises an exponential function of temperature, reflecting a thermally activated process. Therefore, increasing the temperature by a few degrees during the pre-vulcanization step increases the pre-vulcanization rate. For example, pre-vulcanization at room temperature may be about 3-5 days or as much as about 9 days, while pre-vulcanization at, for e.g., about 50-70° C., may take about 3-7 hours. In the absence of pre-vulcanization of the synthetic polyisoprene particles, crosslinking predominantly occurs in the periphery (i.e., case-hardening) of the synthetic polyisoprene particles, resulting in weak particles. Attempts to crosslink the inter-particle region within the particles only during post-vulcanization, discussed below, results in over crosslinking of the intra-particle regions, which, in turn, results in a latex product with poor stretch properties.

The post-vulcanization composition includes amorphous or polysulfur, which is insoluble at latex emulsion temperature, e.g. 20-40° C., but is soluble at a vulcanization or cure temperature, e.g., 110-150° C. Generally, the post-vulcanization composition comprises accelerators such as, but not limited to, zinc diethyldithiocarbamate (ZDEC), zinc dibutyldithiocarbamate (ZDBC), sodium diethyldithiocarbamate (SDEC), sodium dibutyldithiocarbamate (SDBC), a thiuram compound and a xanthogen. Examples of suitable xanthogens include, but are not limited to, diisopropyl xanthogen polysulphide (DIXP), diisopropyl xanthogen, tetraethylthiuram disulfide, and xanthogen sulfide. DIXP is a suitable xanthogen owing to its polysulphidic donor properties. The post-vulcanization composition may further comprise a thiuram accelerator. An example of a polysulphidic thiuram accelerator is dipentamethylene thiuramtetrasulfide (DPTT). Another example of a thiuram compound is tetrabenzyl thiuram disulfide. Zinc oxide may also be added as an activator.

The post-vulcanization composition provides the ability to crosslink regions between the particles of synthetic polyisoprene or inter-particle regions thereby assuring a high quality substantially uniformly cured synthetic polyisoprene product.

The post-vulcanization composition activates inter-particle cross-linking at a temperature of, e.g., 100-150° C. In addition, post-vulcanization processes also crosslink the synthetic polyisoprene particles with sulfur. Such post-vulcanization results in a more homogeneous latex coating having greater strength and elongation properties. The composition produced is stable for up to approximately 5 days at 20° C. to 25° C. and is useful for a production line.

Table 1 shows at least one exemplary embodiment of a Ziegler-Natta (ZN) catalyzed synthetic polyisoprene resin latex composition for producing a polymeric article. The latex composition is preferably aqueous.

TABLE 1

Formulation - ZN Catalyzed

| Component | Quantity per hundred dry rubber (PHR) |
|---|---|
| Synthetic Polyisoprene Resin ZN (e.g., see Table 2) | 100 |
| Alkyl Aryl Sulphonate | 0.1-0.3 |
| Potassium Caprylate/Potassium Oleate | 0.1-0.46 |
| Polyoxyethylene cetyl/Stearyl Ether | 0.1-0.5 |
| Sulfur | 0.8-1.8 |
| Reactive Zinc Oxide | 0.05-0.5 |
| ZDEC/ZDBC | 0.4-1.0 |
| SDBC/SDEC | 0.05-0.5 |
| DIXP/Diisopropyl Xanthogen/Xanthogen Sulfide | 0.2-0.6 |
| Anti-oxidant | 0.5-1.0 |

Table 2 below shows a comparison of pre-vulcanization behavior of an exemplary anionic polyisoprene and an exemplary Ziegler-Natta catalyzed synthetic polyisoprene resin.

TABLE 2

PI Resins

| Microstructure | Anionic IR | Ziegler-Natta (ZN) |
|---|---|---|
| Median particle size (μm) | Max 1.8 | Max 1.5 |
| Cis-1,4 (% wt) | 92 | 96-97 |
| Trans-1,4 (% wt) | 1.50 | 0.50 |
| 3,4-isomers (% wt) | 6.50 | 2.5-3.5 |
| Macrostructure | Linear | Branched |
| Molecular weight distribution | Narrow | Narrow |
| Avg molecular weight (*$10^6$ g/mol) | 2-3 | 1 |
| Gel (% wt) | Intrinsically nil | 10.0-20.0 |
| Ash (% wt) | 0.05-0.1 | 0.15-3.0 |
| Trace metal content (ppm) | 70 | 400-3000 |
| Stabiliser content (% wt) | 0.05-0.3 | 1 |
| TSC (%) | 63 | 60-64 |
| Viscosity (cps) | 150 | 50-150 |
| pH | 9.5-12.0 | 10.0-12.0 |
| Specific gravity | 0.91 | 0.91 |
| Color | Amber | Light yellow |
| Residual solvent (ppm) | 1500 (0.15%) | 1000 (0.10%) |

The present disclosure further provides a method of forming a synthetic polyisoprene polymeric article. The method comprises disposing an elastomeric coating of a Ziegler-Natta catalyzed polyisoprene material on a former and curing the elastomeric coating to form an elastomeric layer of the polymeric article. The disposing step may comprise dipping a coagulant-free or coagulant coated former in an emulsion of the Ziegler-Natta catalyzed polyisoprene material, which may be an aqueous latex composition according to Table 1 having pre-vulcanized particles, at least once to form a thin layer of latex or elastomeric coating with individual particles of pre-vulcanized synthetic polyisoprene on the surface of the former. The former can be any suitable former as is known in the art. The present inventive composition is particularly useful for layering onto formers for condoms and gloves.

Embodiments of the Ziegler-Natta catalyzed formulations disclosed in Table 1, which may use ZN PI resins of Table 2, as well as other Ziegler-Natta catalyzed formulations, are capable of making condoms that have a lighter color than natural rubber condoms, allowing a greater range of colored condoms to be manufactured, while maintaining similar hardness and tensile strength properties. Furthermore, any residual solvent content in condoms made therefrom is lower, lending to lesser allergenicity. Further still, the allergenicity of condoms made from Ziegler-Natta catalyzed formulations is lower compared with natural rubber and anionic formulations, owing to lesser amounts of accelerators and sulfur. The branched molecular structure of the Ziegler-Natta catalyzed synthetic polyisoprene provides greater strength than linear molecular structure of an anionic catalyst produced latex. The Ziegler-Natta catalyzed synthetic polyisoprene also comprises a greater amount of cis character, e.g., cis-1,4 isomer, of the polyisoprene molecules than the anionic catalyzed polyisoprene, improving the strength properties of products made with Ziegler-Natta catalyzed synthetic polyisoprene.

Also, the exemplary Ziegler-Natta catalyzed formulation of Table 1 has potentially lower total solids content, allowing the manufacture of thinner condoms. And, the exemplary Ziegler-Natta catalyzed formulation of Table 1 has potentially lower viscosities during the dipping processes, allowing thinner condoms to be produced therefrom. Lower viscosities also allow a faster line speed during manufacturing. In at least some embodiments, unlike other condom manufacturing, coagulants may be disposed on condom formers prior to the disposition of a Ziegler-Natta catalyzed polymeric coating on the formers, allowing a stronger condom to be manufactured at similar thicknesses compared with anionic polymerized condom formulations.

Furthermore, the Ziegler-Natta catalyzed formulation of Table 1 produces smaller particle sizes, which allows a thinner film and improve user sensitivity during sexual intercourse and/or glove use. Smaller particles also exhibit improved crosslinking, which improves the process-ability of thinner products. For example, preventing the condom or glove collapse during washing processes and allows powder to coat evenly on both inside and outside and, therefore, reducing defects.

Table 3 lists a typical dipping method for producing a condom using a Ziegler-Natta catalyzed polyisoprene resin that is pre-vulcanized, as described above. A similar method can be created for a synthetic polyisoprene surgical glove.

TABLE 3

First dip (thickness of coating may be controlled by latex viscosity and/or former speed in the dip tank
Drying of the latex coating (60-80° C.; 1-3 min).
Second dip (optional)
Drying of the latex coating (60-80° C.; approx 1-3 min).
Beading/ring formation on the open end of the condom
Drying of the ring and latex coating (70-100° C.; approx 1-3 min)
Curing (110-130°C.; approx 11-15 min)
Leaching (70-80° C.; approx 1-2 min)
Stripping of the condoms from the formers The method of dipping for the condoms using the surfactant-stabilized, pre-vulcanized synthetic polyisoprene latex composition is typically within the 5-day period, e.g., an average lifetime of synthetic polyisoprene latex emulsion tank. A condom former is dipped in the composition in a first dip. The wall thickness of the latex coating is controlled by the viscosity of latex, which is a function of the total solids content of the composition in the dip tank. The speed of movement of the formers while dipping also affects the wall thickness. The latex coating that coats the formers is dried at approximately 60-100° C. for approximately 1-3 minutes. The latex coating on the former is, optionally, dipped again into the composition to apply a second dip coating. The latex coating after the second dip is dried at approximately 60-80° C. for approximately 1-3 minutes. The open end of the condom is rolled to create a bead ring, which is distal to a tip of a closed end of the condom.

The coating can be post-vulcanized by heating the coating, e.g., to about 110 to 150° C. for approximately 8 to 15 minutes, to form an elastomeric layer of a condom. Exemplary embodiments include post-vulcanization that is achieved by heating in an oven at approximately 120° C. for approximately 12 minutes. During this period, the inter-particle regions are cross-linked. The intra-particle regions also undergo further crosslinking, producing a more homogeneous latex product. The condom is optionally leached in water at approximately 70-80° C. for about 1-2 minutes to remove residual surfactants and cross-linking agents from the condom. The condom is then stripped from the former. The latex articles, such as condoms, produced display higher strength and improved stretch, even when a low stereo-regularity synthetic polyisoprene is used. The synthetic polyisoprene articles are free from irritation-causing proteins that cause latex sensitivity issues.

Embodiments according to the disclosure comprise the use of a coagulant solution to wet the former and may include an exemplary aqueous solution of 5% calcium nitrate, although other concentrations are possible as are known to those in the art, such as an aqueous solution ranging in concentration from 6-40% calcium nitrate. Other salts, such as calcium chloride, calcium citrate, aluminum sulfate, and the like and/or mixtures thereof may be used. Furthermore, the coagulant solution may be aqueous, alcoholic, or a mixture of aqueous and alcoholic solutions/solvents. Weaker acid solutions may also be used as coagulants, such as formic acid, acetic acid, and other low pKa acids as are known to those in the art.

Embodiments according to the disclosure comprise the use of pre-vulcanizing and post-vulcanizing methods, the technology of which is disclosed in commonly-assigned U.S. Pat. Nos. 8,087,412; 8,464,719; 9,074,027; and 9,074,029 which are incorporated by reference in entirety. Methods for determining the molecular weight between crosslinks $M_c$ is disclosed in U.S. Pat. Nos. 8,087,412; 8,464,719; 9,074,027; and 9,074,029.

EMBODIMENTS

Embodiment 1

A polymeric article comprising: an elastomeric layer comprising cured synthetic polyisoprene particles that comprise a Ziegler-Natta catalyzed polyisoprene material.

Embodiment 2

The polymeric article of the preceding embodiment, wherein the synthetic polyisoprene particles are pre-vulcanized.

Embodiment 3

The polymeric article of any preceding embodiment, wherein the Ziegler-Natta catalyzed polyisoprene material comprises a branched macrostructure.

Embodiment 4

The polymeric article of any preceding embodiment, wherein the Ziegler-Natta catalyzed polyisoprene material comprises a cis-1,4 isomer content of 95% by weight or greater.

Embodiment 5

The polymeric article of any preceding embodiment, wherein the Ziegler-Natta catalyzed polyisoprene material comprises a cis-1,4 isomer content of about 96% to 97% by weight.

Embodiment 6

The polymeric article of any preceding embodiment, wherein the Ziegler-Natta catalyzed polyisoprene material comprises a trans-1,4 isomer content of 1% by weight or less.

Embodiment 7

The polymeric article of any preceding embodiment, wherein the Ziegler-Natta catalyzed polyisoprene material comprises a 3,4 isomer content of 5% by weight or less.

Embodiment 8

The polymeric article of any preceding embodiment, wherein the article has a thickness in the range of from 0.030 to 0.065 mm.

Embodiment 9

The polymeric article of any preceding embodiment, wherein the elastomeric layer comprises a post-vulcanized structure having a molecular weight between crosslinks (Mc) of less than 11,000 g/mol.

Embodiment 10

The polymeric article of any preceding embodiment, wherein the synthetic polyisoprene particles have a median particle diameter in the range of approximately from 0.2 to 2 micrometers, or the synthetic polyisoprene particles have a median particle diameter in the range of approximately from 0.2 to 1.5 micrometers.

Embodiment 11

The polymeric article of any preceding embodiment, wherein the synthetic polyisoprene particles are bonded to each other through intra-polyisoprene particle crosslinks and inter-polyisoprene particle crosslinks.

Embodiment 12

The polymeric article of any preceding embodiment in the form of a condom.

Embodiment 13

A condom comprising: an elastomeric layer comprising cured synthetic polyisoprene particles that are pre-vulcanized, wherein the synthetic polyisoprene particles comprise a Ziegler-Natta catalyzed polyisoprene material that comprises: a cis-1,4 isomer content of 95% by weight or greater; a trans-1,4 isomer content of 1% by weight or less; and a 3,4 isomer content of 5% by weight or less.

Embodiment 14

The condom of the preceding embodiment, wherein the elastomeric layer forms an open end, a closed end, and a tubular sheath extending from the closed end to the open end.

Embodiment 15

The condom of any of embodiment 13 to the preceding embodiment, wherein the Ziegler-Natta catalyzed polyisoprene material comprises a branched macrostructure.

Embodiment 16

The condom of any of embodiment 13 to the preceding embodiment, wherein the elastomeric layer comprises a post-vulcanized structure having a molecular weight between crosslinks (Mc) of less than 11,000 g/mol.

Embodiment 17

The condom of any of embodiment 13 to the preceding embodiment, wherein the synthetic polyisoprene particles have a median particle diameter in the range of approximately from 0.2 to 1.5 micrometers.

Embodiment 18

The polymeric article of any of embodiment 13 to the preceding embodiment, wherein the synthetic polyisoprene particles are bonded to each other through intra-polyisoprene particle crosslinks and inter-polyisoprene particle crosslinks.

Embodiment 19

A method for producing a polymeric article, comprising: disposing an elastomeric coating of a Ziegler-Natta catalyzed polyisoprene material on a former; and curing the elastomeric coating to form an elastomeric layer of the polymeric article.

Embodiment 20

The method of the preceding embodiment, wherein the disposing of the elastomeric coating on the former comprises dipping the former into an emulsion of the Ziegler-Natta catalyzed polyisoprene material.

Embodiment 21

The method of any of embodiment 19 to the preceding embodiment, wherein the emulsion of the Ziegler-Natta catalyzed polyisoprene material is pre-vulcanized before dipping the former.

Embodiment 22

The method of any of embodiment 19 to the preceding embodiment, wherein the polymeric article comprises a condom and the elastomeric layer forms an open end, a closed end, and a tubular sheath extending from the closed end to the open end.

Embodiment 23

The method of any of embodiment 19 to the preceding embodiment, wherein the synthetic polyisoprene particles are bonded to each other through intra-polyisoprene particle crosslinks and inter-polyisoprene particle crosslinks.

EXAMPLES

Condoms according to a formulation of Table 1 were produced.

A method of measuring molecular weight distribution and calculating crosslink density requires cutting of disks from condom samples and swelling the disk samples in toluene until equilibrium. The disks were initially weighed and after swelling they are weighed again. The equilibrium volume fraction of the swelled rubber was calculated using equation shown below. In this equation $P_r$ is the density of rubber (0.92 g/cm$^3$), $P_s$ is the density of toluene (0.862 g/cm$^3$), $W_r$ is the weight of rubber before swelling and $W_s$ is the weight of swelled rubber.

$$WrPrWrPr+Ws-WrPs$$

The volume fraction was used in the Florey-Rehner equation shown below to calculate the crosslink density. In this equation n is the crosslink density, $V_s$ is the molar volume of toluene the swelling solvent which is 106.3 cm3/mol, $V_r$ is the volume fraction of the rubber phase in the swollen gel, and x is the toluene-cis polyisoprene interaction parameter, which is 0.39.

$$n=-1/Vs \text{ multiplied by } [ln(1-Vr)+Vr+x\ Vr2][Vr13-0.5\ Vr]$$

The molecular weight between crosslinks was calculated by the following equation.

$$Mc=Prn$$

Example 1

Table 4 shown below reports measured molecular weight between crosslinks and corresponding crosslink density for several of synthetic polyisoprene condoms manufactured according the embodiments of the subject disclosure. The higher the molecular weight between crosslinks, the lower the crosslink density becomes.

The data presented indicates that the process of the present disclosure results in synthetic polyisoprene condoms that have very consistent molecular weight between crosslinks, providing a condom having adequate mechanical properties. The molecular weight between crosslinks ($M_c$) for the condoms according to the present embodiments is 0.0000845 mol/cm$^3$, which is comparable to that of natural rubber, which has a crosslink density of 0.0000159 mol/cm$^3$.

TABLE 4

| | | | Molecular Weight | | | |
|---|---|---|---|---|---|---|
| Sample | Original weight, mg | Average Swollen weight, mg | Vr | Average Vr | N | Mc g/mol |
| 1 | 76.1 | 460.8 | 0.1564 | 0.1564 | 8.452 × 10$^{-5}$ | 10886 |
| 2 | 76.3 | 448.1 | 0.1613 | | | |
| 3 | 74.9 | 467.6 | 0.1516 | | | |

Figure 1:
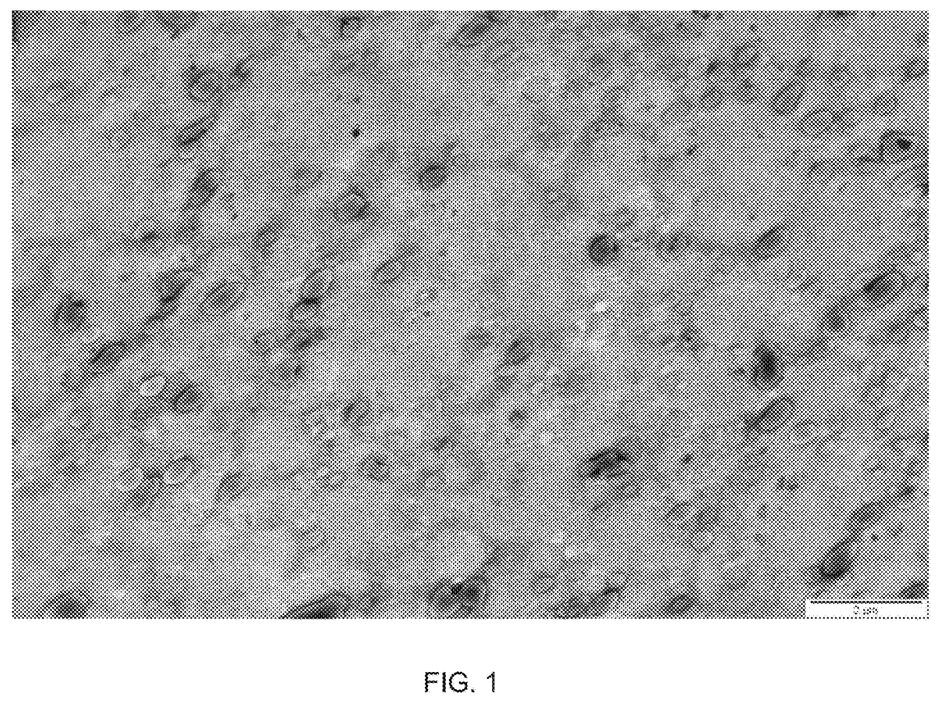
FIG. 1 depicts a first transmission electron microscopy (TEM) image, according to embodiments of the disclosure.

FIG. 1 depicts a first transmission electron microscopy (TEM) image of a surface of a condom, according to embodiments of the disclosure.

Figure 2:
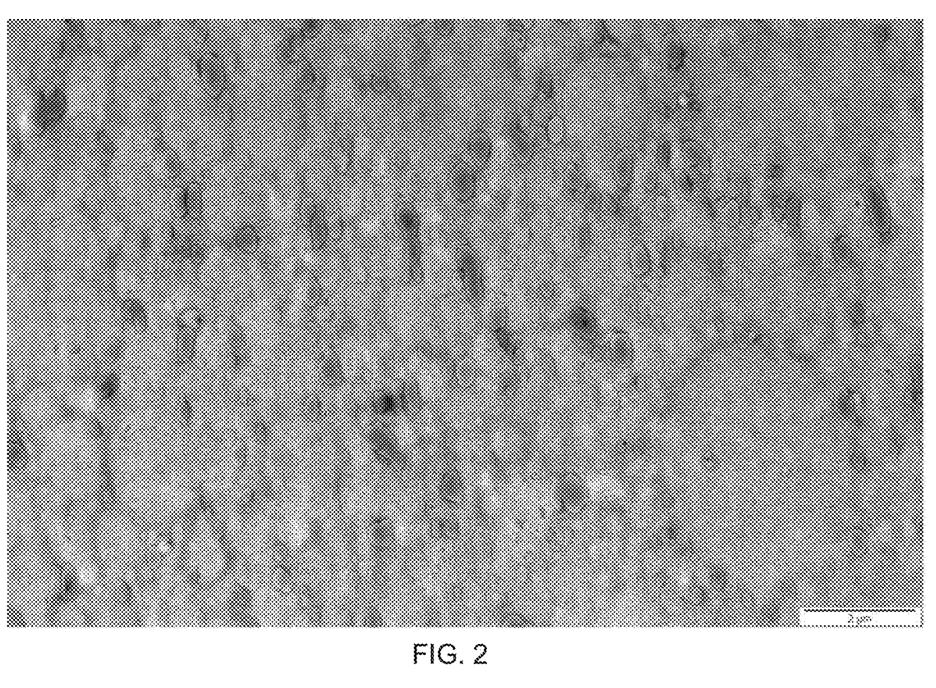
FIG. 2 depicts a second TEM image, according to embodiments of the disclosure.
Figure 3:
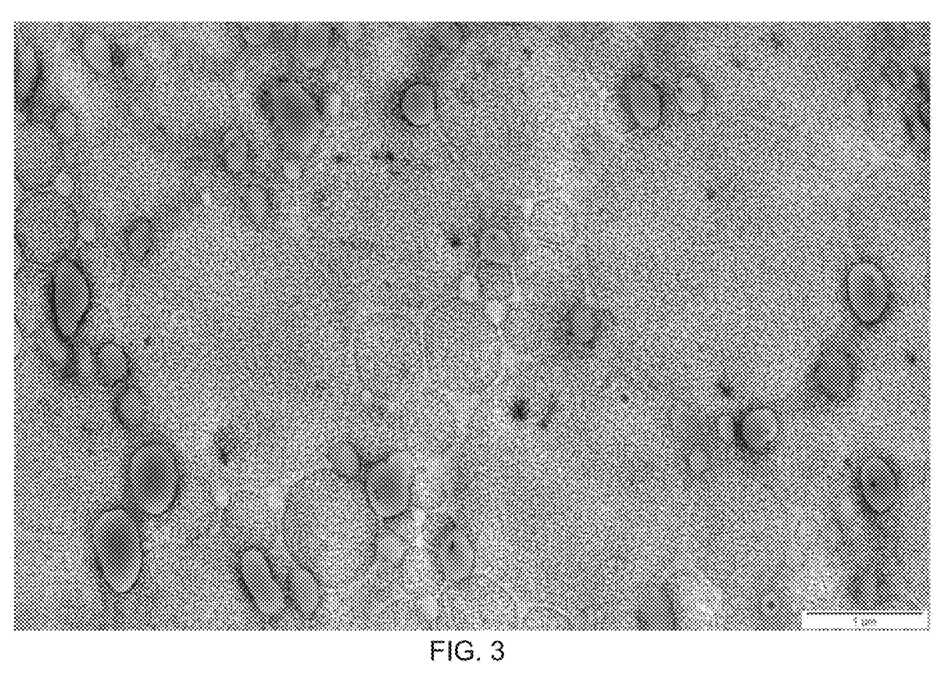
FIG. 3 depicts a third TEM image, according to embodiments of the disclosure.
Figure 4:
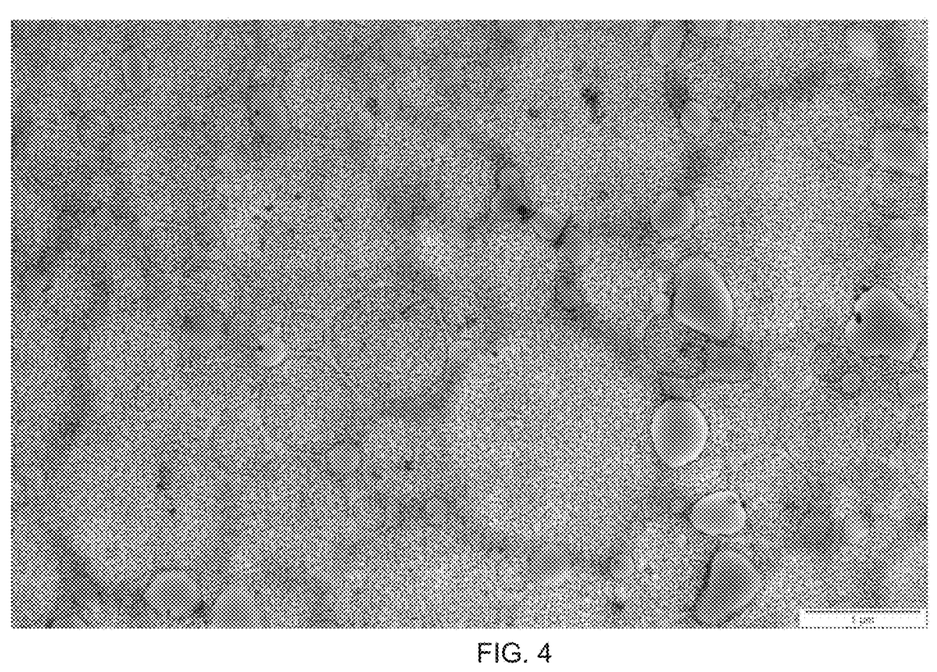
FIG. 4 depicts a fourth TEM image, according to embodiments of the disclosure.

FIG. 2 depicts a second TEM image of a surface of a condom, according to embodiments of the disclosure;

FIG. 3 depicts a third TEM image of a surface of a condom, according to embodiments of the disclosure; and FIG. 4 depicts a fourth TEM image of a surface of a condom, according to embodiments of the disclosure.

The condoms studied in the first, second, third, and fourth TEM images were prepared as follows. Each condom was washed in propan-2-ol to remove the lubricant and then dipped in propan-2-ol containing a small amount of talc to prevent adhesion and thus also facilitate handling. The condom was then air-dried. A number of rings were cut from the condom using a parallel, twin-blade cutter with the blades a nominal 10 mm apart. These rings were to be used for the two methods of analysis: network visualization by TEM and Vr measurement by equilibrium swelling.

Network visualization. After extraction overnight in acetone, the sample of condom was swelled to equilibrium in styrene. The sample was then transferred to gelatin capsules and polymerized by heating. Ultra-thin sections were then prepared by ultramicrotomy at room temperature using glass knives. The sections were collected on a water-filled though and relaxed with xylene vapor before collecting on TEM grids. The sections were then stained with osmium tetroxide vapor for one hour. Osmium tetroxide reacts with carbon-carton double bonds and therefore shows up the rubber network as darker than the polystyrene. Representative TEM micrographs are provided (see TEM16803-6) in FIGS. 1-4.

The latex particles were fairly closely bonded together but the boundaries between the particles could often be seen. The samples also contain many voids, i.e. areas where the styrene has infiltrated to form a large pale area. Some of these voids contain small dark particles so it seems likely that most or all of them are caused by styrene forming pools around these particles which have not bonded to the rubber. A void which appears to be empty may actually contain a particle which is not visible because it was either above or below the section.

There are also some small dark patches inside some of the rubber particles. These do not look like particles but seem to be small areas of the rubber network which have some electron-dense (i.e. high atomic number) material attached to them.

The uncertainty on the scalebar dimension is ±10% in all of the TEM micrographs.

The latex particles, i.e., synthetic polyisoprene particles catalyzed using Ziegler-Natta catalysts, exhibited close bonding.

All numerical values recited herein are exemplary, are not to be considered limiting, and include ranges therebetween, and can be inclusive or exclusive of the endpoints. Optional included ranges can be from integer values therebetween, at the order of magnitude recited or the next smaller order of magnitude. For example, if the lower range value is 0.1, optional included endpoints can be 0.2, 0.3, 0.4 . . . 1.1, 1.2, and the like, as well as 1, 2, 3 and the like; if the higher range is 10, optional included endpoints can be 7, 6, and the like, as well as 7.9, 7.8, and the like.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

It is to be understood that various changes and modifications to the embodiments described herein will be apparent to those skilled in the art. Such changes and modifications can be made without departing from the spirit and scope of the present disclosure and without demising the attendant advantages. It is, therefore, intended that such changes and modifications be covered by the appended claims.

All references, including publications, patent applications, and patents, cited herein are hereby incorporated by reference to the same extent as if each reference were individually and specifically indicated to be incorporated by reference and were set forth in its entirety herein.

The invention claimed is:

1. A polymeric article comprising:
    an elastomeric layer comprising cured synthetic polyisoprene particles that comprise a Ziegler-Natta catalyzed polyisoprene material;
    wherein the elastomeric layer comprises a post-vulcanized structure having a molecular weight between crosslinks ($M_c$) of less than 11,000 g/mol.

2. The polymeric article of claim 1, wherein the synthetic polyisoprene particles are pre-vulcanized.

3. The polymeric article of claim 1, wherein the Ziegler-Natta catalyzed polyisoprene material comprises a branched macrostructure.

4. The polymeric article of claim 1, wherein the Ziegler-Natta catalyzed polyisoprene material comprises a cis-1,4 isomer content of 95% by weight or greater.

5. The polymeric article of claim 1, wherein the Ziegler-Natta catalyzed polyisoprene material comprises a cis-1,4 isomer content of about 96% to 97% by weight.

6. The polymeric article of claim 1, wherein the Ziegler-Natta catalyzed polyisoprene material comprises a trans-1,4 isomer content of 1% by weight or less.

7. The polymeric article of claim 1, wherein the Ziegler-Natta catalyzed polyisoprene material comprises a 3,4 isomer content of 5% by weight or less.

8. The polymeric article of claim 1, wherein the article has a thickness in the range of from 0.030 to 0.065 mm.

9. The polymeric article of claim 1, wherein the synthetic polyisoprene particles have a median particle diameter in the range of approximately from 0.2 to 2 micrometers.

10. The polymeric article of claim 1, wherein the synthetic polyisoprene particles are bonded to each other through intra-polyisoprene particle crosslinks and inter-polyisoprene particle crosslinks.

11. A condom comprising:
    an elastomeric layer comprising cured synthetic polyisoprene particles that are pre-vulcanized,
    wherein the synthetic polyisoprene particles comprise a Ziegler-Natta catalyzed polyisoprene material that comprises:
        a cis-1,4 isomer content of 95% by weight or greater;
        a trans-1,4 isomer content of 1% by weight or less; and
        a 3,4 isomer content of 5% by weight or less
    wherein the elastomeric layer comprises a post-vulcanized structure having a molecular weight between crosslinks ($M_c$) of less than 11,000 g/mol.

12. The condom of claim 11, wherein the elastomeric layer forms an open end, a closed end, and a tubular sheath extending from the closed end to the open end.

13. The condom of claim 11, wherein the Ziegler-Natta catalyzed polyisoprene material comprises a branched macrostructure.

14. The condom of claim 11, wherein the synthetic polyisoprene particles have a median particle diameter in the range of approximately from 0.2 to 1.5 micrometers.

15. A method for producing a polymeric article, comprising:
    disposing an elastomeric coating of a Ziegler-Natta catalyzed polyisoprene material on a former; and
    curing the elastomeric coating to form an elastomeric layer of the polymeric article wherein the elastomeric layer comprises a post-vulcanized structure having a molecular weight between crosslinks ($M_c$) of less than 11,000 g/mol.

16. The method of claim 15, wherein the disposing of the elastomeric coating on the former comprises dipping the former into an emulsion of the Ziegler-Natta catalyzed polyisoprene material.

17. The method of claim 16, wherein the emulsion of the Ziegler-Natta catalyzed polyisoprene material is pre-vulcanized before dipping the former.

18. The method of claim 15, wherein the polymeric article comprises a condom and the elastomeric layer forms an open end, a closed end, and a tubular sheath extending from the closed end to the open end.

* * * * *